(12) United States Patent
Goldstein

(10) Patent No.: US 9,498,597 B2
(45) Date of Patent: Nov. 22, 2016

(54) DEVICE FOR INSTILLATION OF A CHEMICAL AGENT INTO THE ENDOMETRIAL CAVITY FOR PURPOSE OF GLOBAL ENDOMETRIAL ABLATION

(71) Applicant: Apex Gynocological Instruments, LLC, New York, NY (US)

(72) Inventor: Steven R. Goldstein, New York, NY (US)

(73) Assignee: Apex Gynocological Instruments, LLC., New York, NY (US)

( * ) Notice: Subject to any disclaimer, the term of this patent is extended or adjusted under 35 U.S.C. 154(b) by 0 days.

(21) Appl. No.: 14/406,921

(22) PCT Filed: Jun. 13, 2013

(86) PCT No.: PCT/US2013/045566
§ 371 (c)(1),
(2) Date: Dec. 10, 2014

(87) PCT Pub. No.: WO2013/188619
PCT Pub. Date: Dec. 19, 2013

(65) Prior Publication Data
US 2015/0141963 A1    May 21, 2015

Related U.S. Application Data

(60) Provisional application No. 61/659,151, filed on Jun. 13, 2012.

(51) Int. Cl.
*A61M 31/00*   (2006.01)
*A61M 5/00*    (2006.01)
(Continued)

(52) U.S. Cl.
CPC .......... *A61M 25/0082* (2013.01); *A61B 17/42* (2013.01); *A61M 5/31* (2013.01);
(Continued)

(58) Field of Classification Search
CPC ..................... A61B 17/42; A61B 2017/00893; A61B 2017/4216; A61M 2025/0004;
(Continued)

(56) References Cited

U.S. PATENT DOCUMENTS

| 3,645,265 A | * | 2/1972 | Majzlin | ............... | A61B 18/1485 |
| | | | | | 128/840 |
| 5,891,457 A | | 4/1999 | Neuwirth | | |

(Continued)

OTHER PUBLICATIONS

International Search Report and Written Opinion issued on Sep. 2, 2013 in International Application No. PCT/US2013/045566.

(Continued)

*Primary Examiner* — Jason Flick
(74) *Attorney, Agent, or Firm* — Stroock & Stroock & Lavan, LLP.

(57) ABSTRACT

A device for chemical endometrial ablation comprising an outer tube, a moveable cervical collar surrounding a portion of the outer tube and located near the distal end of the outer tube, an inner tube movable in a distal-proximal direction within the lumen of the outer tube, a porous and/or sponge-like material on the distal end of the inner tube within the lumen of the distal end of the outer tube having a size, shape, and expandability so that when the distal end of the inner tube within the distal end of the outer tube is moved in a distal direction in relation to the outer tube, the porous and/or sponge-like material expands to the approximate size of a uterus so as to contact the endometrium, a source of cauterizing agent, and means to cause the cauterizing agent to flow through the lumen of the inner tube onto the porous and/or sponge-like material. In operation, the cervical collar can be moved or advanced along the outer tube to the cervix and secured tightly around the external portio in order to prevent chemical cauterizing agent from entering the vagina.

10 Claims, 2 Drawing Sheets

(51) Int. Cl.
*A61M 25/00* (2006.01)
*A61B 17/42* (2006.01)
*A61M 5/31* (2006.01)
*A61B 17/00* (2006.01)

(52) U.S. Cl.
CPC ..... *A61M 31/00* (2013.01); *A61B 2017/00893* (2013.01); *A61B 2017/4216* (2013.01); *A61M 2025/0004* (2013.01); *A61M 2025/0008* (2013.01); *A61M 2025/0018* (2013.01); *A61M 2202/0468* (2013.01); *A61M 2210/1433* (2013.01)

(58) Field of Classification Search
CPC ............. A61M 2025/0008; A61M 2025/0018; A61M 2202/0468; A61M 2210/1433; A61M 25/0082; A61M 31/00; A61M 5/31
USPC ........................................................ 604/515
See application file for complete search history.

(56) References Cited

U.S. PATENT DOCUMENTS

| | | | |
|---|---|---|---|
| 6,066,132 A * | 5/2000 | Chen .................. | A61B 18/08 604/530 |
| 2003/0049302 A1* | 3/2003 | Pauletti ............... | A61K 9/0036 424/430 |
| 2005/0288660 A1 | 12/2005 | Ryan et al. | |
| 2008/0058797 A1 | 3/2008 | Rioux | |
| 2009/0069883 A1 | 3/2009 | Ding et al. | |
| 2009/0138000 A1 | 5/2009 | Vancelette et al. | |
| 2010/0087798 A1* | 4/2010 | Adams ................ | A61B 1/303 604/515 |

OTHER PUBLICATIONS

Extended European Search Report issued on Nov. 19, 2015 in European Patent Application No. 13803886.4.

* cited by examiner

DEVICE FOR INSTILLATION OF A CHEMICAL AGENT INTO THE ENDOMETRIAL CAVITY FOR PURPOSE OF GLOBAL ENDOMETRIAL ABLATION

CROSS-REFERENCE TO RELATED APPLICATIONS

This application is a national stage application under 35 U.S.C. 371 based on and claiming the benefit of International Application Serial No. PCT/US2013/045566, filed on Jun. 13, 2013, which claims the benefit of priority from U.S. Provisional Application No. 61/659,151, filed on Jun. 13, 2012, the entire contents of each of which are incorporated herein by reference.

BACKGROUND OF THE INVENTION

This invention relates to the field of endometrial ablation. More specifically the invention relates to devices and methods for performing endometrial ablations with chemical cauterizing agents.

According to current insurance company policies, endometrial ablation is considered medically necessary for women who meet certain selection criteria, including A. menorrhagia unresponsive to either 1. dilation and currettage or 2. hormonal therapy or other pharmacotherapy; and B. endometrial sampling has excluded cancer, pre-cancer, or structural abnormalities that require surgery; and C. pap smear and gynecologic examination have excluded significant cervical disease. Chemical ablation with trichloroacetic acid, cryoablation, electrosurgical ablation, laser, microwave endometrial ablation, radiofrequency ablation, and thermoablation are alternative approaches are considered by certain insurance companies to be medically appropriate and established.

Kucukozkan, et al., *Chemical ablation of endometrium with trichloroacetic acid, Int J Gynaecol Obstet.,* 84(1):41-6, January 2004, concluded that endometrial ablation by trichloroacetic acid (TCA) may readily be performed as an alternative treatment method in the management of dysfunctional uterine bleeding (DUB).

However, except for the aforementioned Kucukozkan, et al., experiments in Turkey, the use of chemical cauterizing agent for endometrial ablation has not been carried out in clinical settings and has not been adopted by clinicians at all in the U.S. It is believed that Kucukozkan, et al., used cotton swabs to apply the chemical cauterizing agent to the endometrium in their experiments. To the inventor's knowledge, no special devices have been proposed or used by others to deliver a chemical cauterizing agent into the endometrial cavity.

There are numerous advantages to delivering a chemical cauterizing agent to the endometrial surface as a method of global endometrial ablation rather than currently available devices that require various energy sources, significant anesthesia, and/or direct visualization with hysteroscopy in order to ablate the endometrium.

SUMMARY OF THE INVENTION

In one aspect, the invention comprises a device for chemical endometrial ablation comprising an outer tube, a cervical collar surrounding a portion of the outer tube on the outer tube and moveable in relation to the outer tube, an inner tube movable in a distal-proximal direction within the lumen of the outer tube, a porous and/or sponge-like material on the distal end of the inner tube within the lumen of the distal end of the outer tube having a size, shape, and expandability property so that when the distal end of the inner tube within the distal end of the outer tube is moved in a distal direction in relation to the outer tube, the porous and/or sponge-like material exits the outer tube and expands to the approximate size of a uterus so as to contact the endometrium, a source of cauterizing agent, and means to cause the cauterizing agent to flow through the lumen of the inner tube onto the porous and/or sponge-like material.

In the retracted, or insertion position, the porous and/or sponge-like material is compressed within the lumen of the outer tube. In the expanded position, when the inner tube is moved distally in relation to the outer tube, the porous and/or sponge-like material expands to fill the uterine cavity and contact the endometrium to apply the chemical cauterizing agent.

The volume of the sponge when expanded can be 3 to 12 cc in preferred embodiments. The volume of the sponge when expanded can be different, depending on operator preference or expected volume of the uterus to be chemically ablated.

Preferably, the device comprises an outer tube having a lumen, a proximal end, a distal end, and an inner diameter, a cervical collar surrounding a portion of the outer tube on the outer tube and moveable in relation to the outer tube, an inner tube having an outer diameter less than the inner diameter of the outer tube, the inner tube movable in a distal-proximal direction within the lumen of the outer tube, the inner tube having a proximal end and a distal end, a porous and/or sponge-like material on the distal end of the inner tube within the lumen of the distal end of the outer tube, the porous and/or sponge-like material having a size, shape, and expandability so that when the distal end of the inner tube within the distal end of the outer tube is moved in a distal direction in relation to the outer tube, the porous and/or sponge-like material expands to the approximate size of a uterus having an endometrium so as to contact the endometrium of the uterus, a source of cauterizing agent at the proximal end of the inner tube, and means to cause the cauterizing agent to flow through the lumen of the inner tube onto the porous and/or sponge-like material.

The preferred cauterizing agent is trichloroacetic acid. Derivatives of trichloroacetic acid such as bichloroacetic acid, silver nitrate, and derivatives of silver nitrate can also be used in certain embodiments.

The porous and/or sponge-like material preferably conforms to the contours of the uterus so that the cauterizing agent will effectively contact the endometrium when it is received by the porous and/or sponge-like material from the cauterizing agent source such as a syringe.

In embodiments where the source is a syringe, the syringe can be pre-filled with the cauterizing agent or it can be filled with cauterizing agent by the operator. It is preferred to have a pre-filled syringe attached to the proximal end to avoid the need to attach it by the operator but in embodiments wherein the syringe is pre-filled, a valve or other device is preferably provided to prevent cauterizing agent from exiting the syringe until the distal end of the device is inserted into a uterus and the porous and/or sponge-like material has expanded.

The outer tube can have markings to allow the operator to gauge the depth of insertion into the uterine cavity.

The moveable cervical collar is designed to prevent leakage of chemical cauterizing agent from the uterus and to retain the chemical within the uterus. In operation, the cervical collar is moved or advanced along the outer tube to the cervix and can be secured tightly around the external portio in order to prevent chemical cauterizing agent from entering the vagina. The collar can comprise means to tighten it on the external portio of the cervix such as a drawstring or the like.

DETAILED DESCRIPTION OF THE INVENTION

Figure 1:
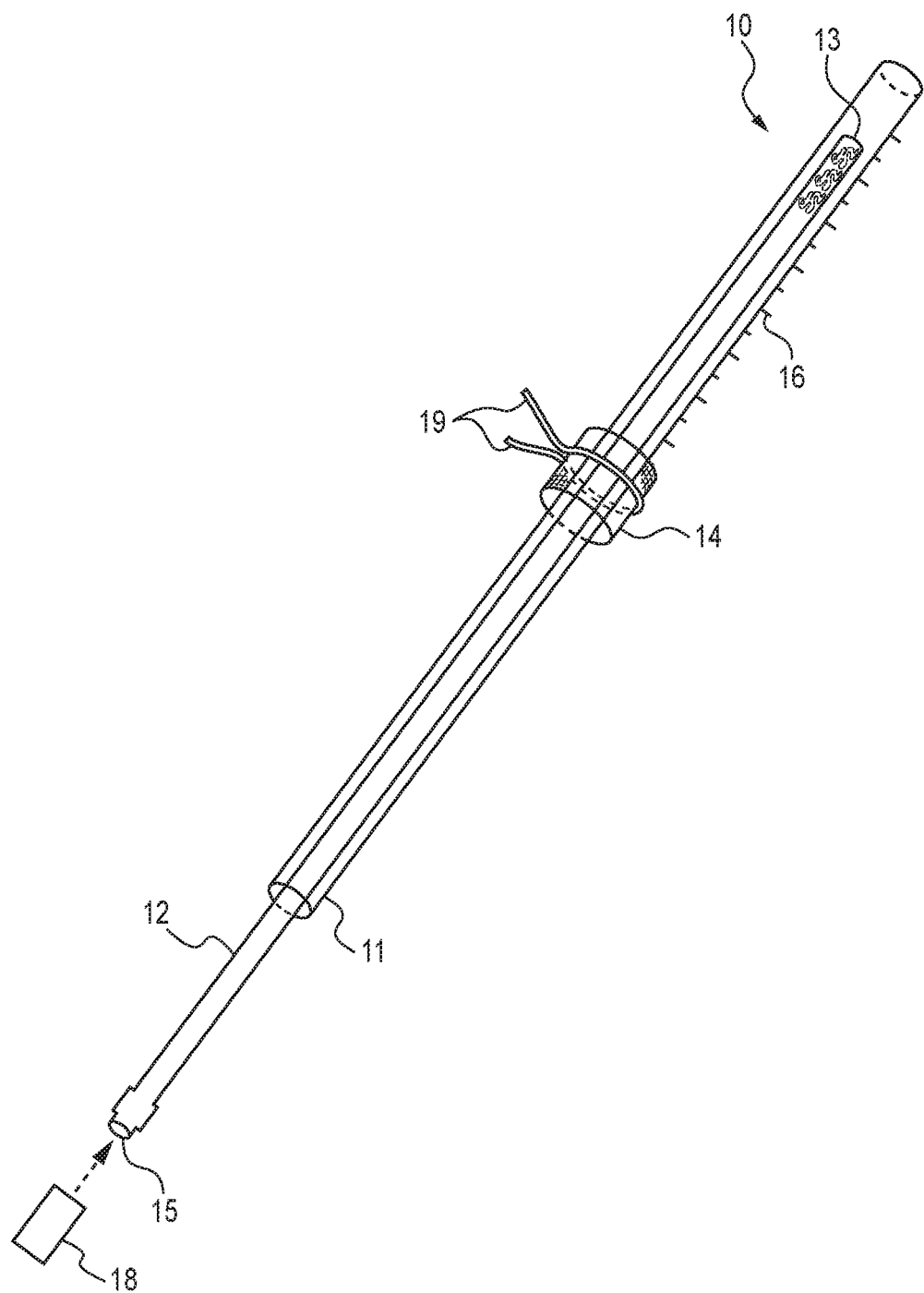
FIG. 1 is a perspective view of one embodiment of a device according to the invention in a retracted state.

Referring to FIG. 1, an embodiment of the device 10 is illustrated which consists of an outer tube 11, an inner tube 12 within the lumen of the outer tube, a sponge-like material 13 at the distal end of the inner tube 12 and fluidly connected thereto. A syringe 18 is separately provided to fit into the opening 15 at the proximal end of the inner tube shown in this embodiment. The syringe 18 is filled with trichloroacetic acid (not shown), although other sources and species of chemical can be used, for example derivatives of trichloroacetic acid such as dichloroacetic acid, silver nitrate, or derivatives of silver nitrate.

Figure 2:
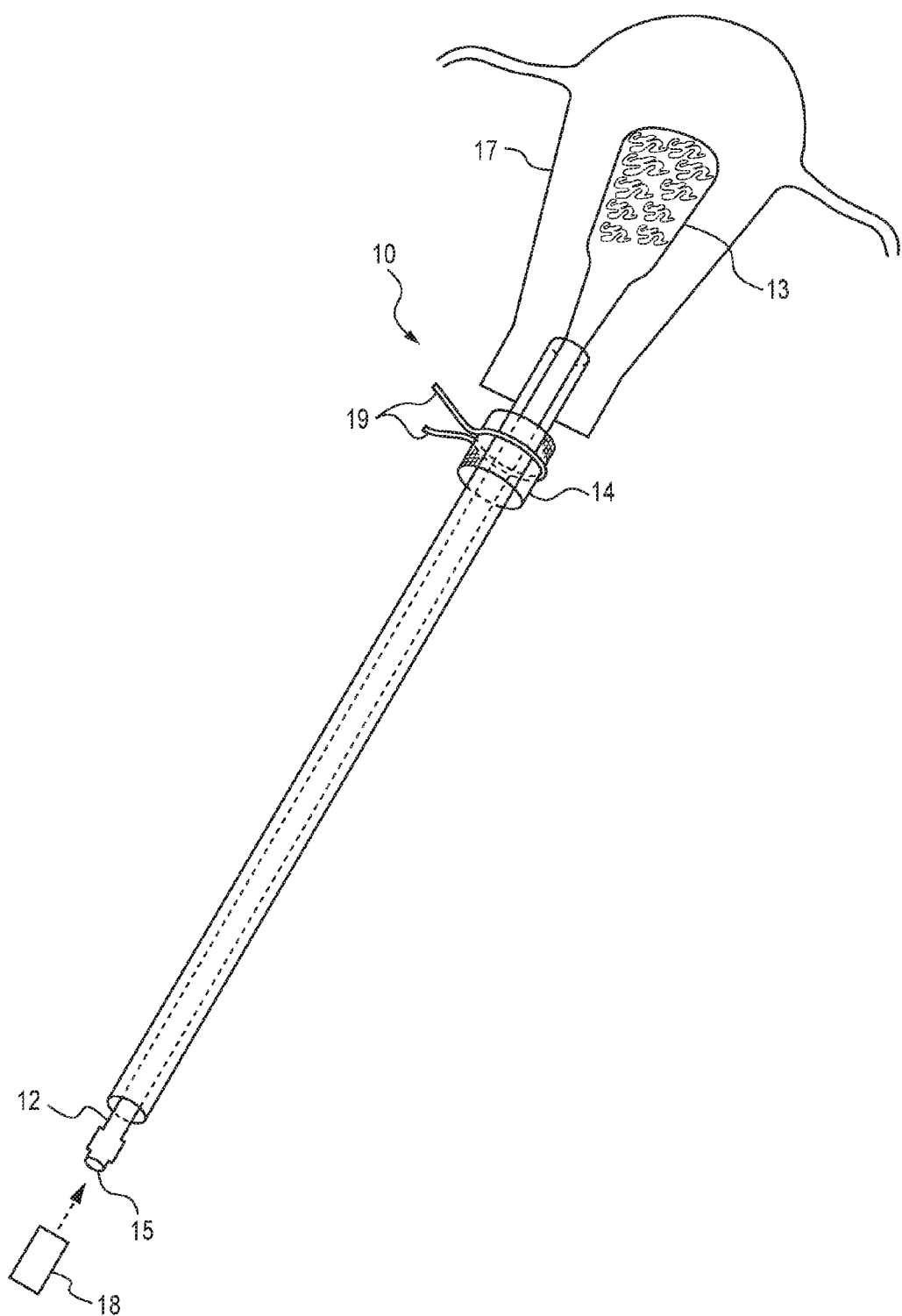
FIG. 2 is a perspective view of the embodiment of FIG. 1 in an expanded state.

The device is designed to be passed through the cervix into the endometrial cavity (17 in FIG. 2). The plastic and porous and/or sponge-like material used in the device are of the type which are approved for human contact.

A collection collar 14 is then advanced along the shaft of the catheter to the cervix and can be approximated tightly around the external portio to accommodate variations in cervical size and anatomy in order to minimize the possibility of runback. The collar may also be lined with an absorptive fiber, in the event of any small amount of leakage.

The sponge-like material 13 may have a single or multiple openings so as to allow adequate diffusion of the chemical cauterant to spread evenly through the endometrial cavity 17, thus insuring uniform adequate ablation. The proximal end 15 of the catheter receives a syringe 18 either by screwing into the proximal end 15 of inner tube 12 or by pressure fitting into proximal end 15. The syringe 18, which fits into opening 15, is pre-filled with the chemical cauterant to obviate any operator handling of the caustic material. A drawstring 19 can be used to tighten the collar 14.

The outer tube 11 has one half cm markings 16 in the illustrated embodiment to allow the operator to gauge the depth of insertion into the uterine cavity.

The pre-filled syringe 18 securely locks on to the catheter, with a snug adherence of the delivery system to the portio of the cervix and no reliance upon power source for completion of the ablation.

The porous sponge like material 13 is "swedged-on" to the distal end of the inner tube 12.

Referring now to FIG. 2, when the outer tube 11 is retracted proximately and/or the inner tube 12 is moved distally in relation to the outer tube 11, the sponge-like material 13 springs open, conforming to the contours of the endometrial surface of the uterus 17. The chemical cauterant is contained within a pre-loaded, closed syringe system 18. A pre-calculated volume of chemical cauterant is injected to adequately saturate the sponge which is in direct contact with the endometrial surface for a specified period of time.

After application of the cauterant chemical to the endometrial surface, the porous and/or sponge-like material 13 is then pulled back to be retracted into the outer sheath, the cervical collar loosened slightly, withdrawn and then further cinched closed to prevent any liquid from escaping during final removal through the vagina.

The distal tip of the device may have a single or multiple openings so as to allow adequate diffusion of the chemical cauterant to spread evenly through the endometrial cavity, thus insuring uniform adequate ablation. The proximal end 15 of the catheter 12 attaches to a syringe 18 pre-filled with the chemical cauterant to obviate any operator handling of the caustic material.

The insertion catheter has one half cm markings 16 to allow the operator to gauge the depth of insertion into the uterine cavity.

The unique features of this device include the safety-designed catheter, pre-filled syringe that securely locks on to the catheter, the snug adherence of the delivery system to the portio of the cervix and no reliance upon power source for completion of the ablation.

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

What is claimed is:

1. A device for chemical endometrial ablation comprising:
   an outer tube having a lumen, a proximal end, a distal end, and an inner diameter;
   a cervical collar surrounding a portion of the outer tube on the outer tube and moveable in a distal-proximal direction along the outer tube, the collar configured to fit around the external portio of a cervix;
   an inner tube having a lumen, a proximal end, a distal end, and an outer diameter less than the inner diameter of the outer tube, the inner tube movable in a distal-proximal direction within the lumen of the outer tube;
   a sponge comprising a porous material on the distal end of the inner tube and compressed within the lumen of the distal end of the outer tube, the sponge having a size, shape, and expandability configured to match the approximate size and shape of a uterine cavity and conform to the contours of the endometrial surface of the uterus when the distal end of the inner tube is moved in a distal direction to exit the lumen of the outer tube; and
   a delivery system containing a cauterizing agent secured to an opening at the proximal end of the inner tube, the delivery system configured to deliver the cauterizing agent through the lumen of the inner tube and through the pores of the sponge.

2. The device of claim 1 wherein the cauterizing agent is trichloroacetic acid or its derivatives or silver nitrate or its derivatives.

3. The device of claim 1 wherein the delivery system comprises a syringe fluidly connected to the proximal end of the inner tube.

4. The device of claim 1 wherein the outer tube has markings to allow an operator to gauge depth of insertion into the uterine cavity.

5. The device of claim 1 wherein the cervical collar is lined with an absorptive fiber.

6. The device of claim 1 wherein the cervical collar comprises means to secure the collar to the portio of the cervix to prevent the chemical cauterizing agent from exiting the uterus and entering the vagina.

7. The device of claim 6 wherein the means to secure the collar comprises a drawstring.

8. The device of claim 1 wherein the cauterizing agent is trichloroacetic acid.

9. A method for chemical endometrial ablation comprising: providing a device according to claim 1, moving the distal end of the inner tube in a distal direction in relation to the outer tube, causing the sponge to exit the lumen of the outer tube and expand to contact the endometrial surface of the uterus; causing the cauterizing agent to flow through the lumen of the inner tube and through the pores of the sponge onto the endometrial surface; and moving the distal end of the inner tube in a proximal direction in relation to the outer tube, retracting the sponge back into the distal end of the outer tube.

10. The device of claim 1 wherein the delivery system is configured to prevent the cauterizing agent from exiting the delivery system before the sponge is expanded in the uterine cavity.

* * * * *